United States Patent [19]

Kuroda et al.

[11] 4,215,584
[45] Aug. 5, 1980

[54] METHOD FOR TRANSMISSION AND RECEPTION OF ULTRASONIC BEAMS USING ULTRASONIC TRANSDUCER ELEMENT ARRAY

[75] Inventors: Masao Kuroda, Nishioizumimachi; Hiroshi Kanda, Hachioji, both of Japan

[73] Assignee: Hitachi Medical Corporation, Japan

[21] Appl. No.: 831,137

[22] Filed: Sep. 7, 1977

[30] Foreign Application Priority Data

Sep. 8, 1976 [JP] Japan ............................ 51/106650

[51] Int. Cl.$^2$ ............................................ G01N 29/04
[52] U.S. Cl. ............................ 73/626; 367/105; 128/660
[58] Field of Search .......... 128/2 V, 2.05 Z, 660–663; 340/1 R, 5 MD; 73/618–626; 367/105

[56] References Cited

U.S. PATENT DOCUMENTS

| | | | |
|---|---|---|---|
| 3,675,472 | 7/1972 | Kay et al. | 73/626 X |
| 3,693,415 | 9/1972 | Whittington | 73/626 X |
| 3,820,387 | 6/1974 | Grabendorfer et al. | 73/626 X |
| 3,911,730 | 10/1975 | Niklas | 73/619 |
| 3,919,683 | 11/1975 | Itamura et al. | 340/1 R |
| 4,005,382 | 1/1977 | Beaver | 340/1 R |
| 4,058,003 | 11/1977 | Macovski | 128/2 V X |
| 4,064,741 | 12/1977 | Reynolds | 73/626 |
| 4,070,642 | 1/1978 | Iinuma et al. | 73/620 X |
| 4,161,122 | 7/1979 | Buchner | 128/660 |
| 4,164,213 | 8/1979 | Höelzler | 128/660 |

OTHER PUBLICATIONS

Maginness, M. G. et al. "State-of-the-Art in 2D Ultrasonic Transducer Array Technology", Med. Physics v. 3, No. 5, Sep./Oct. 1976.
Burkhardt, C. B. et al., "Focussed Ultrasound Over a Large Depth with an Annular Transducer-an Alternative Method", IEE Trans Sonics & Ultrasonics vol. SU-22, pp. 11–15, Jan. 1975.

Primary Examiner—Robert W. Michell
Assistant Examiner—Francis J. Jaworski
Attorney, Agent, or Firm—Craig & Antonelli

[57] ABSTRACT

Disclosed is a method for transmission and reception of ultrasonic beams using an array of ultrasonic transducer elements in which a plurality of transducer element sets each including the selected number of transducer elements for the transmission and/or reception of ultrasonic beams are sequentially selected. First and second sets having different focal axes defined relative to the plane of the transducer array are selected for the transmission and reception modes of operation respectively during the production of a single scan line. The position of at least one of the transducer elements in the first set is different from those of the transducer elements in the second set.

11 Claims, 9 Drawing Figures

METHOD FOR TRANSMISSION AND RECEPTION OF ULTRASONIC BEAMS USING ULTRASONIC TRANSDUCER ELEMENT ARRAY

FIELD OF THE INVENTION

This invention relates to a method for transmission and reception of ultrasonic beams and more particularly to a method for electronically controlling an array of ultrasonic transducer elements.

DESCRIPTION OF THE PRIOR ART

Recently, ultrasonic diagnostic techniques have been developed which need either anatomization of the body under observation nor examination of blood. Especially, the so-called B scope or scan for obtaining ultrasonic diagnostic images employs the electronic scanning of ultrasonic beams for imaging at high speed.

Figure 1:
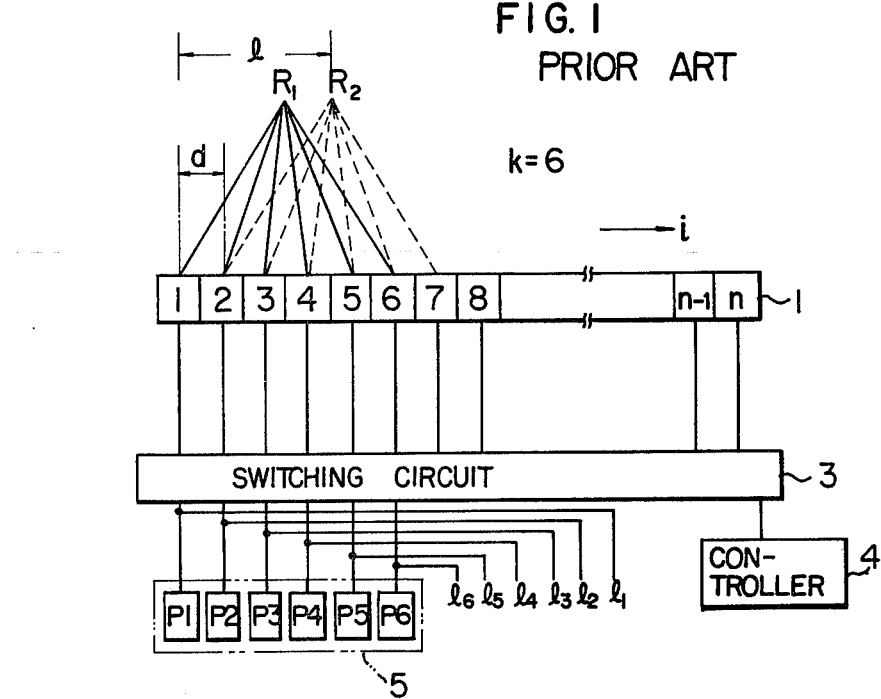
FIGS. 1 to 3 show block diagrams of conventional ultrasonic beam scanners.

A conventionally used linear electronic scanning type ultrasonic beam scanner is diagrammatically shown in FIG. 1. An ultrasonic transducer 1 includes an array of n ultrasonic transducer elements No. 1 to No. n arranged with a pitch of d. The transducer elements No. 1 to No. n are connected with a switching circuit 3 which in turn receives a control signal from a controller 4 to selectively connect pulses P1 to P6 in a pulser group 5 with the elements in the transducer 1.

The operation of the switching circuit 3 will now be explained. Assuming that a set of k transducer elements are simultaneously excited, FIG. 1 exemplifies the case of k=6. When it is desired to excite a set of elements No. 1 to No. 6, the switching circuit 3 operates to connect the pulses P1 to P6 with the elements No. 1 to No. 6, respectively. As a result, the elements No. 1 to No. 6 are excited by the pulsers P1 to P6 so that the ultrasonic beams transmitted from these elements are focussed on a point R1 as indicated by solid lines. Next, a set of elements No. 2 to No. 7 are connected with the pulsers P1 to P6 by the changing-over action of the switching circuit 3. The elements No. 2 to No. 7 are thus excited to emit ultrasonic beams to be focussed on a point R2 as indicated by dotted lines. Similarly, subsequent sets of transducer elements are scanned sequentially along the transducer element array or the transducer 1 through the switching circuit 3 by the controller 4. It is noted that the same set of transducer elements are used for both the transmission and reception modes of operation of the transducer 1. In the reception mode, electric signals based on the ultrasonic beams reflected from an object are obtained from lines $l_1$ to $l_6$.

In general, when k elements counted from the i-th element are excited, the switching circuit 3 operates to connect the pulsers and the transducer elements so that the jth pulser $P_j$ (j=1~k) is connected with the (j+i−1)th element. In that case, a distance l along the transducer element array from the 1st element to a focal point of ultrasonic beams transmitted by the k elements countered from the i-th element is represented by the following equation:

$$l = \left(\frac{k-1}{2} + i - 1\right)d$$

From this equation, it will be understood that a linear scanning at intervals of d along the transducer element array can be attained by varying i.

The focal point of transmitted ultrasonic beams lies on an extension line of the boundary between the adjacent transducer elements when k is an even number as shown in FIG. 1 (k=6 in the illustrated example). When k is an odd number as shown in FIG. 2 (k=5 in the illustrated example), the focal point lies on an extension line of the center of one transducer element.

Figure 2:
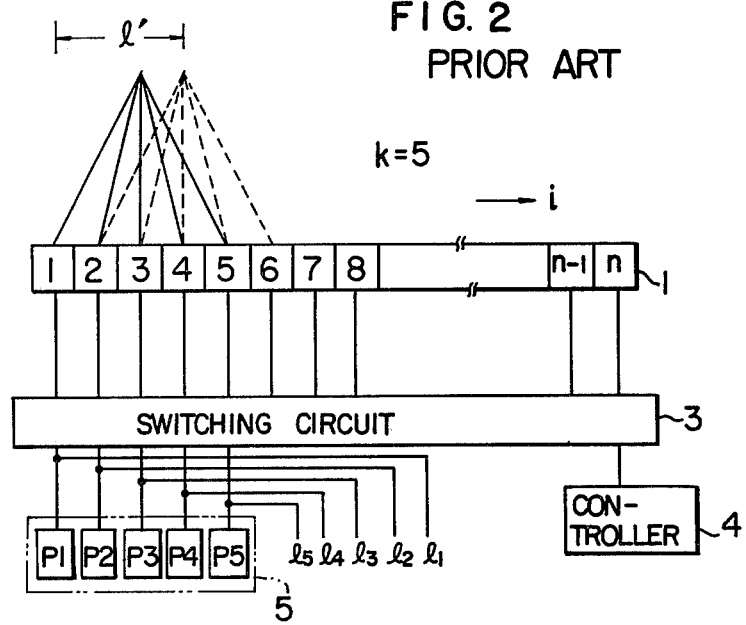

It will be understood that the combination of the scanning operations shown in FIGS. 1 and 2 can provide a linear scanning at intervals of d/2 or half of the pitch of one element along the transducer element array. Such a scanning system is shown in FIG. 3.

Figure 3:
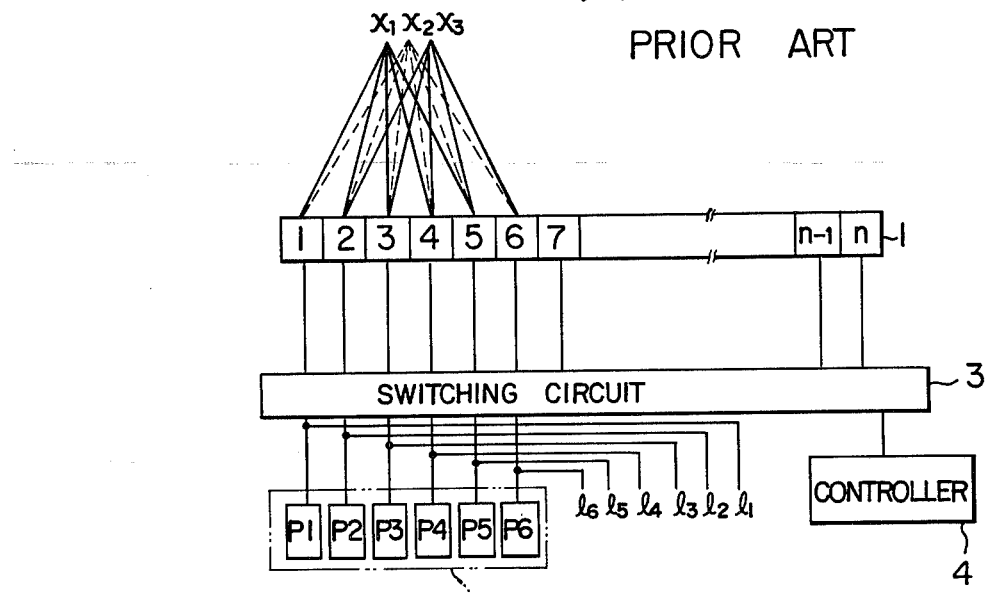

The system of FIG. 3 has the same construction as that of FIG. 1 but the operation of the switching circuit 3 of FIG. 3 is somewhat different from that of FIG. 1. First, the switching circuit 3 operates to connect the pulsers P1 to P5 in the pulser group 5 with the elements No. 1 to No. 5 in the transducer 1. These elements are excited to emit ultrasonic beams which in turn are focussed on a point $x_1$. Next, the circuit 3 operates to connect the pulsers P1 to P6 with the elements No. 1 to No. 6 which emit ultrasonic beams to be focussed on a point $x_2$ advanced from the focal point $x_1$ by d/2. Next, the circuit 3 operates to connect the pulsers P1 to P5 with the elements No. 2 to No. 6 which emit ultrasonic beams to be focussed on a point $x_3$ advanced from the focal point $x_2$ by d/2. It is noted that the same set of transducer elements are used for both the transmission and reception modes.

Thus, such a method permits a linear scanning at intervals of d/2 or the half of one element pitch. However, further fine scanning is impossible in this method.

SUMMARY OF THE INVENTION

An object of the invention is to provide a method for transmission and reception of ultrasonic beams using an array of ultrasonic transducer elements, in which an intermediate directivity characteristic between the directivity characteristics of transmitted and received ultrasonic beams can be realized.

Another object of the invention is to provide a method for scanning ultrasonic beams at a scanning pitch smaller than the pitch with which the transducer elements are arranged.

According to the invention, different sets of transducer elements having different focal axes defined relative to the plane of the transducer array are used for the transmission and reception modes respectively to produce a single scan line so that different directivity characteristics are provided between the transmission and reception modes to enjoy the combined characteristic thereof.

DESCRIPTION OF THE PREFERRED EMBODIMENTS

Figure 4A:
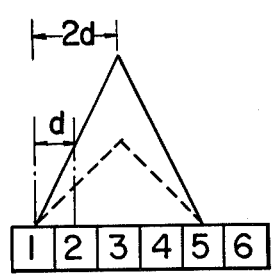
FIGS. 4A to 4D show block diagrams for explaining the principle of the invention.
Figure 4B:
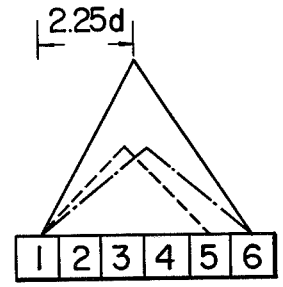
Figure 4C:
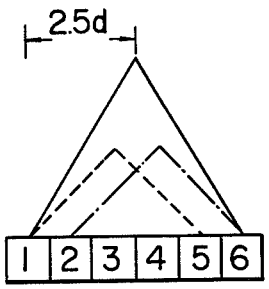
Figure 4D:
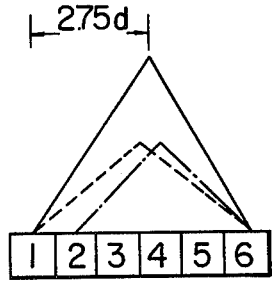

FIGS. 4A to 4D show block diagrams for explaining the principle of a method according to the invention. FIG. 4A illustrates the case where the same transducer elements No. 1 to No. 5 are excited for both the transmission and reception modes to produce a single scan line. As indicated by a dotted line, the directivity characteristic of transmitted ultrasonic beams is the same as that of received beams. The total or combined directivity characteristic is distributed at a location distanced from the 1st element by $2d$, as indicated by a solid line. FIG. 4B illustrates the case where the elements No. 1 to No. 5 and No. 1 to No. 6 having different focal or symmetry axes defined relative to the plane of the transducer array are selected for the transmission and reception modes respectively to produce a single scan line. The directivity characteristics of transmitted and received beams are indicated by dotted and chained lines, respectively. The total characteristic is distributed at a location distanced by $2.25d$ ($=2\frac{1}{4}d$), as indicated by a solid line. FIG. 4C illustrates that during the production of a single scan line the elements No. 1 to No. 5 and No. 2 to No. 6 having different focal axes are selected for the transmission and reception modes respectively to provide a total characteristic which is distributed at a location distanced by $2.5d$ ($=2\ 2/4d$). FIG. 4D illustrates the case where during the production of a single scan line the elements No. 1 to No. 6 and No. 2 to No. 6 having different focal axes are selected for the transmission and reception modes respectively to provide a total characteristic which is distributed at a location distanced by $2.75d$ ($=2\frac{3}{4}d$). The same characteristic may be provided by using the elements No. 1 to No. 6 for both the transmission and reception modes.

Thus, it will be understood that the use of the scanning manners shown in FIGS. 4A to 4D permits a linear scanning at intervals of $d/4$ or a quarter of the pitch of one element along the transducer element array thereby to produce a plurality of scan lines.

When the directivity of received beams is shifted from that of transmitted beams to provide an intermediate directivity, some problems must be considered which include the widening or narrowing of beam width, the deterioration of sensitivity and the increase of side-lobes. All of these problems depend upon the widening or narrowing of the width of transmitted beams or the width of received beams and the amount of shift between the transmitted and received beams. In connection with the beam width, it should be noted that FIGS. 4A to 4D only show the beams illustratively and the illustrated triangles do not correspond to the actual beam width.

Figure 5:
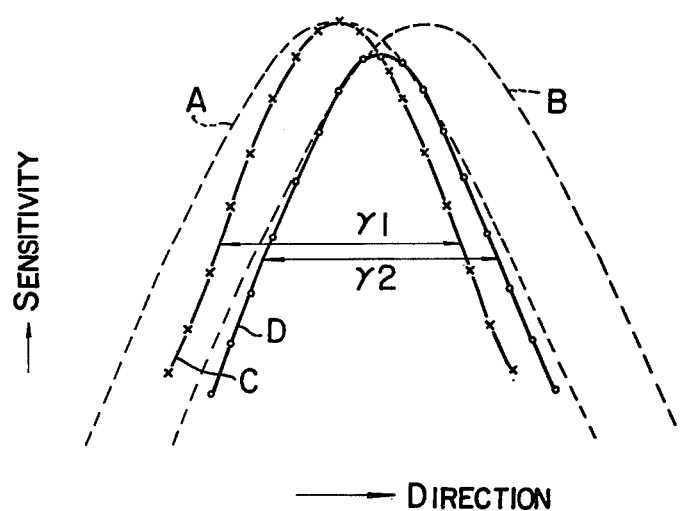
FIG. 5 shows characteristic curves obtained by simulation experiments for indicating the effects of the invention.

In order to ascertain the extent of the above problems, experiments on simulation have been conducted using actual ultrasonic beams. FIG. 5 shows the results of the experiments. Dotted curves represent the directivity of the transmitted or received beam. When no shift existed between the directivities of transmitted and received beams as represented by curve A, the total directivity represented by curve C was obtained. On the other hand, when a shift existed between the directivity of transmitted beam (curve A) and that of received beam (curve B), the total or intermediate directivity represented by curve D was obtained. From FIG. 5, it can be understood that the widening or narrowing of half-width (or the full width of half maximum) $\gamma$ as well as the deterioration of sensitivity offer no practical problem if the amount of shift in directivity is relatively small in comparison with the beam width. In the shown example, though the directivity of the received beam was shifted from that of the transmitted beam by about $\frac{1}{4}$ of the half-width of beam, the deterioration of sensitivity was below 10% and the change of half-width $\gamma$ was almost never observed.

The application of the method of the invention to practical usages has revealed that the deterioration of sensitivity, the change of half-width, and the increase of the side-lobe ratio are practically negligible.

Figure 6:
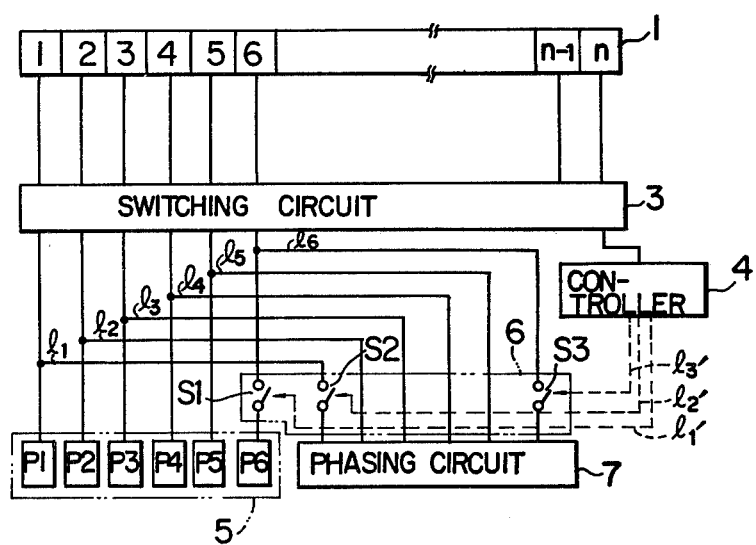
FIG. 6 shows a block diagram of a system embodying the invention.

Next, a system embodying the method of the invention will be explained referring to FIG. 6. In a manner similar to FIGS. 1 to 3, the switching circuit 3 operates to change over the connection of the pulsers P1 to P6 in the pulser group 5 with the transducer elements No. 1 to No. n in the transducer 1 under a condition controlled by the controller 4. The transducer elements are excited to emit ultrasonic beams for transmission in response to the outputs of the associated pulsers and receive the ultrasonic beams reflected from an object. Electric signals based on the received beams are supplied to a phasing circuit 7 through lines $l_1$ to $l_6$. The system also includes a switch group 6 having a switch S1 provided at the output side of the pulser P6 and switches S2 and S3 provided in the way of the lines $l_1$ and $l_6$. The switches S1 to S3 are controlled through lines $l_1'$ to $l_3'$ by control signals from the controller 4 as shown in Table I which illustrates the scheme of scanning employed in the system of FIG. 6. In Table I, "0" and "1" labelled with respect to each respective switch represent the turned-off and turned-on conditions of the switch.

Table I

|  |  | Sequence of Scanning | | | |
|---|---|---|---|---|---|
|  |  | I | II | III | IV |
| Switch | S1 | "0" | "0" | "0" | "1" |
|  | S2 | "1" | "1" | "0" | "0" |
|  | S3 | "0" | "1" | "1" | "1" |
| Number of Elements | Transmission | 5 | 5 | 5 | 6 |
|  | Reception | 5 | 6 | 5 | 5 |

In operation, the switching circuit 3 first selects the elements No. 1 to No. 6 so as to connect them with the pulsers P1 to P6, respectively. At the same time, the switches S1 to S3 are controlled by the control signals from the controller 4 as shown by the first scanning step I in Table I. Namely, the pulser P6 is disabled by the switch 51 and only the switch S2 is turned on so that the 5 element transmission and reception modes of operation as shown in FIG. 4A are carried out. Thereafter, the switches S2 and S3 are turned on in accordance with the second scanning step II of Table I so that the elements No. 1 to No. 5 and No. 1 to No. 6 are selected for the transmission and reception modes respectively to provide such an operation as shown in FIG. 4B. Next, or in the third scanning step III, the switch 3 is turned on so that the elements No. 1 to No. 5 and No. 2 to No. 6 are selected for the transmission and reception modes respectively to provide such an operation as shown in FIG. 4C. In the fourth scanning step IV, the switches S1 and S3 are turned on so that the elements No. 1 to No. 6 and No. 2 to No. 6 are selected for the transmission and reception modes respectively to provide such an operation as shown in FIG. 4D.

Thus, a linear scanning at intervals of the pitch of a quarter of one element over a distance corresponding to the pitch of one element can be made by selecting the elements No. 1 to No. 6 in accordance with the scanning steps I to IV.

Next, the switching circuit 3 selects the elements No. 2 to No. 7 and the above-described scanning steps I to IV are repeated. Similar linear scannings are sequentially carried out along the transducer element array from one end thereof to the other end.

Though the invention has been described and shown with respect to the specified embodiment, various changes or modifications can be made.

For example, six elements can be used for both the transmission and reception modes in the scanning step III while all the switches S1 to S3 are turned on.

Instead of using the switches S1 to S3, the switching circuit 3 and the controller 4 may be modified to provide the same effect.

Further, the transmitter and receiver transducer elements are reversible with each other. As a result, the same effect can be obtained.

Though the specified number of transmitter or receiver transducer elements has been exemplified, any suitable number of elements can be used for the transmission and reception modes.

In accordance with the invention, a linear scanning at smaller intervals, for example, at intervals of a quarter of the pitch of one element is possible. Therefore, the number of transducer elements can be greatly reduced in comparison with the conventional systems to obtain a performance equivalent thereto.

We claim:

1. A method for transmission and reception of ultrasonic beams using a linear array of plural ultrasonic transducer elements, focal axes of transmitted ultrasonic beams being respectively defined relative to the planes of transducer element sets each of which includes a selected number of ultrasonic transducer elements, said method during the production of a single scan line comprising:
    a step of simultaneously exciting the transducer elements of a first transducer element set to transmit ultrasonic beams from the transducer elements of said first transducer element set to a point on a first focal axis defined by said first transducer element set; and
    a step of receiving said ultrasonic beams transmitted from said first transducer element set and reflected from an object by the transducer elements of a second transducer element set which defines a second focal axis different in position relative to the plane of the array than said first focal axis.

2. A method according to claim 1, wherein the number of transducer elements constituting said first set is different from that of transducer elements constituting said second set.

3. A method according to claim 1, wherein the number of transducer elements constituting said first set is the same as that of transducer elements constituting said second set, and the position of at least one of the transducer elements constituting said first set is different from those of the transducer elements constituting said second set.

4. In a method for transmission and reception of ultrasonic beams comprising a step of transmitting ultrasonic beams, from an array of plural ultrasonic transducer elements arranged on a line and a step of receiving the ultrasonic beams by the transducer array, thereby to produce a plurality of scan lines,
    the improvement in that the production of a single scan line includes the step of simultaneously transmitting ultrasonic beams from a first set of transducer elements in the transducer array along a first focal axis to an object and the step of simultaneously receiving, the ultrasonic beams transmitted from said first set of transducer elements and reflected from said object, by a second set of transducer elements in the transducer array, said second set having a focal axis defined relative to the plane of the array which differs from the focal axis of said first set.

5. A method according to claim 4, wherein the second set includes part of the transducer elements of the first set and at least one transducer element other than the transducer elements of the first set.

6. A method according to claim 4, wherein said array is linear.

7. In a method for transmission and reception of ultrasonic beams comprising a step of transmitting ultrasonic beams from an array of plural ultrasonic transducer elements arranged on a line and a step of receiving the ultrasonic beams by the transducer array, thereby to produce a plurality of scan lines,
    the improvement in that the production of successive single scan lines includes the step of simultaneously transmitting ultrasonic beams from a first set of transducer elements in the transducer array to an object, the step of simultaneously receiving, the ultrasonic beams transmitted from said first set of transducer elements and reflected from said object, by said first set of transducer elements in the transducer array to produce a first single scan line, the step of again simultaneously transmitting ultrasonic beams from said first set of transducer elements to said object, and the step of simultaneously receiving, the ultrasonic beams transmitted from said first set of transducer elements and reflected from said object, by transducer elements of a second set of transducer elements different from said first set of transducer elements to produce the next single scan line.

8. A method according to claim 7, wherein a combined directivity characteristic of the transmission and reception beams moves an increment along the line on which the transducer elements are arranged which increment is equal to d/4, where d equals the pitch provided between each adjacent transducer element.

9. A method according to claim 7, wherein the second set of transducer elements has a focal axis defined relative to the plane of the array which differs from the focal axis of the first set of transducer elements defined relative to the plane of the array.

10. A method according to claim 7, wherein said array is linear.

11. A method according to claim 7, wherein after reception on said second set of transducers the method further comprises the step of again simultaneously transmitting ultrasonic beams from said first set of transducers to said object, the step of simultaneously receiving the ultrasonic beams transmitted from the first set of transducer elements and reflected from said object by transducer elements of a third set of transducer elements different from said first and said second set of transducer elements to produce the next successive single scan line, the step of simultaneously transmitting ultrasonic beams from said second set of transducer elements in the transducer array to said object, the step of simultaneously receiving ultrasonic beams transmitted from said second set of transducer elements and reflected from said object by transducer elements of said third set of transducer elements to produce the next successive single scan line, the step of again simultaneously transmitting ultrasonic beams from said second set of transducer elements in the transducer array to said object, and the step of simultaneously receiving ultrasonic beams transmitted from said second set of transducer elements in the transducer array and reflected from said object, whereby the combined directivity characteristic of the transmission and reception beams moves in increments along the line on which the transducer elements are arranged which increments are equal to d/4, where d equals the pitch provided between each adjacent transducer element.

* * * * *